(12) United States Patent
Marczak et al.

(10) Patent No.: US 10,983,035 B2
(45) Date of Patent: Apr. 20, 2021

(54) SIMULTANEOUS ISOLATION AND PRECONCENTRATION OF EXOSOMES BY ION CONCENTRATION POLARIZATION METHOD AND APPARATUS

(71) Applicant: University of Notre Dame du Lac, South Bend, IN (US)

(72) Inventors: Steven Marczak, Notre Dame, IN (US); Zeinab Ramshani, Notre Dame, IN (US); Reginald Hill, Granger, IN (US); David B. Go, Granger, IN (US); Hsueh-Chia Chang, Granger, IN (US); Satyajyoti Senapati, Notre Dame, IN (US)

(73) Assignee: University of Notre Dame du Lac, South Bend, IN (US)

( * ) Notice: Subject to any disclaimer, the term of this patent is extended or adjusted under 35 U.S.C. 154(b) by 257 days.

(21) Appl. No.: 16/290,439

(22) Filed: Mar. 1, 2019

(65) Prior Publication Data
US 2019/0271619 A1 Sep. 5, 2019

Related U.S. Application Data

(60) Provisional application No. 62/637,209, filed on Mar. 1, 2018.

(51) Int. Cl.
*C12Q 1/6825* (2018.01)
*G01N 1/40* (2006.01)
(Continued)

(52) U.S. Cl.
CPC ...... *G01N 1/4005* (2013.01); *B01L 3/502753* (2013.01); *B01L 3/502761* (2013.01);
(Continued)

(58) Field of Classification Search
CPC ....... B01L 2200/0668; B01L 2300/069; B01L 2400/0421; B01L 2400/0436;
(Continued)

(56) References Cited

U.S. PATENT DOCUMENTS

2018/0346975 A1* 12/2018 Marczak .............. C12Q 1/6832

OTHER PUBLICATIONS

Yang et al., "Exosome separation using microfluidic systems: size-based, immunoaffinity-based and dynamic methodologies," Biotechnol. J. 2017, 12, 1600699.
(Continued)

*Primary Examiner* — Jennifer Wecker
(74) *Attorney, Agent, or Firm* — Greenberg Traurig, LLP

(57) ABSTRACT

Exosomes carry microRNA biomarkers, occur in higher abundance in cancerous patients than in healthy ones, and because they are present in most biofluids, including blood and urine, can be obtained non-invasively. Standard laboratory techniques to isolate exosomes are expensive, time-consuming, provide poor purity, and recover on the order of 25% of the available exosomes. We present a new microfluidic technique to simultaneously isolate exosomes and preconcentrate them by electrophoresis using a high transverse local electric field generated by ion-depleting ion-selective membrane. We use pressure-driven flow to deliver an exosome sample to a microfluidic chip such that the transverse electric field forces them out of the cross flow and into an agarose gel which filters out unwanted cellular debris while the ion-selective membrane concentrates the exosomes through an enrichment effect. We efficiently isolated exosomes from 1×PBS buffer, cell culture media and blood serum. Using flow rates from 150 μL/hr to 200 μL/hr and field strengths of 100 V/cm, we consistently captured between 60% to 80% of exosomes from buffer, cell culture media, and blood serum as confirmed by both fluorescence spectroscopy and nanoparticle tracking analysis. Our micro-
(Continued)

fluidic chip maintained this recovery rate for more than twenty minutes with a concentration factor of 15 for ten minutes of isolation.

16 Claims, 4 Drawing Sheets

(51) Int. Cl.
    *C12Q 1/6806* (2018.01)
    *B01L 3/00* (2006.01)
    *C12Q 1/6886* (2018.01)
(52) U.S. Cl.
    CPC ......... *C12Q 1/6806* (2013.01); *C12Q 1/6825* (2013.01); *C12Q 1/6886* (2013.01); *B01L 2400/0421* (2013.01); *B01L 2400/0436* (2013.01); *B01L 2400/0481* (2013.01); *G01N 2001/4011* (2013.01); *G01N 2001/4038* (2013.01); *G01N 2001/4088* (2013.01)
(58) Field of Classification Search
    CPC ..... B01L 2400/0478; B01L 2400/0481; B01L 3/50273; B01L 3/502753; B01L 3/502761; C12Q 1/6806; C12Q 1/6825; C12Q 1/6886; G01N 1/4005; G01N 2001/4011; G01N 2001/4038; G01N 2001/4088
    See application file for complete search history.

(56) References Cited

OTHER PUBLICATIONS

Zhao et al., "A Microfluidic ExoSearch Chip for Multiplexed Exosome Detection Towards Blod-based Ovarian Cancer Diagnosis," Lab Chip. 2016, 16, 489-496.
Vaidyanathan et al., "Detecting Exosomes Specifically: A Multiplexed Device Based on Alternating Current Electrodynamic Induced Nanoshearing," Anal. Chem. 2014, 86, 11125-11132.
Chen, et al., "Microfluidic isolation and transcriptome analysis of serum microvesicles," Lab Chip. 2010, 10, 505-511.
Wang et al., "Ciliated micropillars for the microfluidic-based isolation of nanoscale lipid vesicles," Lab Chip. 2013, 13, 2879-2882.
Davies et al., "Microfluidic filtration system to isolate extracellular vesicles from blood," Lab Chip. 2012, 12, 5202-5210.
Cho et al., "Isolation of extracellular vesicle from blood plasma using electrophoretic migration through porous membrane," Sens. Actuators B. 2016, 233, 289-297.
Lee et al., "Acoustic Purification of Extracellular Microvesicles," ACS Nano. 2015, 9, 2321-2327.
Marczak et al., "Simultaneous isolation and preconcentration of exosomes by ion concentration polarization," Electrophoresis 2017, 0, 1-11.
Marczak et al., "Induced nanoparticle aggregation for short nucleic acid quantification by depletion isotachophoresis," Biosens. Bioelec. 2016,86, 840-848.
Slouka et al., "Microfluidic Systems with Ion-Selective Membranes," Annu. Rev. Anal. Chem. 2014, 7, 317-335.
Pernodet et al., "Pore size of agarose gels by atomic force microscopy," Electrophoresis, 1997, 18, 55-58.
Righetti et al., "On the Limiting Pore Size of Hydrophilic Gels for Electrophoresis and Isoelectric Focusing," J. Biochem Biophys. Methods. 1981, 4, 347-363.
Taller et al., "On-chip surface acoustic wave lysis and ion-exchange nanomembrane detection of exosomal RNA for pancreatic cancer study and diagnosis," Lab Chip, 2015, 15, 1656-1666.
Weiner, B. B., "Measuring the size and surface charge of exosomes, microvesicles and liposomes," Microvesicles and Liposomes, Application Note, Brookhaven Instruments, A Nova Instruments Company, 2013.
Minerick et al., "Electrokinetic transport of red blood cells in microcapillaries," Electrophoresis, 2002, 23, 2165-2173.
Keller et al., "Body fluid derived exosomes as a novel template for clinical diagnostics," J. Transl. Med. 2011, 9, 86.
Shen et al., "BEAMing and Droplet Digital PCR Analysis of Mutant IDH1 mRNA in Glioma Patient Serum and Cerebrospinal Fluid Extracellular Vesicles," Mol. Ther. Nucleic Acids. 2013, 2, e109.
Chevillet et al., "Quantitative and stoichiometric analysis of the microRNA content of exosomes," Proc. Natl. Acad. Sci. 2014, 111, 14888-14893.
Schultz et al., "MicroRNA Biomarkers in Whole Blood for Detection of Pancreatic Cancer," J. Am. Med. Assoc. 2014, 311, 392-404.
Capello, et al., "Sequential Validation of Blood-Based Protein Biomarker Candidates for Early-Stage Pancreatic Cancer," J. Natl. Cancer Inst. 2017, 109, 266.
Soliman, et al., "Monitoring potential prostate cancer biomarkers in urine by capillary electrophoresis—tandem mass spectrometry," J. Chromatogr. A., 2012, 1267, 162-169.
Patel et al., "High resolution of microRNA signatures in human whole saliva," Arch. Oral Biol. 2011, 56, 1506-1513.
Schneider et al., "Chapter 19—Using Breast Milk to Assess Breast Cancer Risk: The Role of Mass Spectrometry-Based Proteomics," Advancements of Mass Spectrometry in Biomedical Research, Advances in Experimental Medicine and Biology 806, 399-408, 2014.
Arcaro, et al., "Differential Expression of Cancer-Related Proteins in Paired Breast Milk Samples from Women with Breast Cancer," J. Hum. Lact. 2012, 28(4), 543-546.
Swarup et al., "Circulating (cell-free) nucleic acids—A promising, non-invasive tool for early detection of several human diseases," FEBS Lett. 2007, 581, 795-799.
Hao, et al., "Circulating cell-free DNA in serum as a biomarker for diagnosis and prognostic prediction of colorectal cancer," Br. J. Cancer, 2014, 111, 1482-1489.
Zimmermann, et al., Salivary mRNA targets for cancer diagnostics, Oral Oncol. 2008, 44, 425-429.
Debernardi, et al., "Noninvasive urinary miRNA biomarkers for early detection of pancreatic adenocarcinoma," Am. J. Cancer Res. 2015, 5, 3455-3466.
Javidi, et al., "Cell-free microRNAs as cancer biomarkers: The odyssey of miRNAs through body fluids," Med. Oncol. 2014, 31, 295.
Torphy, et al., "Circulating Tumor Cells as a Biomarker of Response to Treatment in Patient-Derived Xenograft Mouse Models of Pancreatic Adenocarcinoma," PLos One. 2014, 9, 89474.
Skog, et al., "Glioblastoma microvesicles transport RNA and protein that promote tumor growth and provide diagnostic biomarkers," Nat. Cell Biol. 2008, 10, 1470-1476.
Minciacchi, et al., "Extracellular Vesicles in Cancer: Exosomes, Microvesicles and the Emerging Role of Large Oncosomes," Semin. Cell Dev. Biol. 2015, 40, 41-51.
Hakulinen, et al., "Secretion of Active Membrane Type 1 Matrix Metalloproteinase (MMP-14) Into Extracellular Space in Microvesicular Exosomes," J. Cell Biochem. 2008, 105, 1211-1218.
Luga, et al., "Exosomes Mediate Stromal Mobilization of Autocrine Wnt-PCP Signaling in Breast Cancer Cell Migration," Cell. 2012, 151, 1542-1556.
Webber, et al., "Differentiation of Tumour Promoting Stromal Myofibroblasts by Cancer Exosomes," Oncogene. 2015, 34, 319-331.
Kahlert, et al., "Identification of Doublestranded Genomic DNA Spanning All Chromosomes with Mutated KRAS and p53 DNA in the Serum Exosomes of Patients with Pancreatic Cancer," J. Biol. Chem. 2014, 289, 3869-3975.
Lee, et al., "Barriers to horizontal cell transformation by extracellular vesicles containing oncogenic H-ras," Biochem. Biophys. Res. Commun. 2014, 451, 295-301.
Hoshino, et al., "Tumour exosome integrins determine organotropic metastasis," Nature. 2015, 527, 329-335.
Lv et al., "Exosomes mediate drug resistance transfer in MCF-7 breast cancer cells and a probable mechanism is delivery of P-glycoprotein," Tumor Biol. 2014, 35, 10773-10779.

(56) References Cited

OTHER PUBLICATIONS

Choi et al., "Extracellular vesicles shed from gefitinib-resistant nonsmall cell lung cancer regulate the tumor microenviroment," Proteomics. 2014, 14, 1845-1856.
Yu et al., "Tumor-derived exosomes in cancer progression and treatment failure," Oncotarget. 2015, 6 , 37151-37168.
Tickner et al., "Functions and therapeutic roles of exosomes in cancer," Front Onco. 2014, 4, 127.
Peinado et al., "Melanoma exosomes educate bone marrow progenitor cells toward a pro-metastatic phenotype through MET," Nat. Med. 2012, 18, 883-891.
Grange et al., "Microvesicles Released from Human Renal Cancer Stem Cells Stimulate Angiogenesis and Formation of Lung Premetastatic Niche," Tumor Stem Cell Biol. 2011, 71, 5346-5356.
Milane et al., "Exosome mediated communication within the tumor microenvironment," J. Control Release 2015, 219, 278-294.
Ray, K., Nat. Rev. Gastroenterol Hepatol. 2015, 12, 371.
Zhang et al., "Microenvironment-induced PTEN loss by exosomal microRNA primes brain metastasis outgrowth," Nature 2015, 527, 100-104.
Richards et al., "Cancer-Associated Fibroblast Exosomes Regulate Survival and Proliferation of Pancreatic Cancer Cells," Oncogene 2017, 36, 1770-1778.
Taylor et al., "MicroRNA signatures of tumor-derived exosomes as diagnostic biomarkers of ovarian cancer," Gynecol Oncol. 2008, 110, 13-21.
Rabinowits et al., "Exosomal MicroRNA: A Diagnostic Marker for Lung Cancer," Clin. Lung Cancer. 2009, 10, 42-48.
Michael et al., "Exosomes from human saliva as a source of microRNA biomarkers," Oral Diseases 2010, 16, 34-38.
Zhou et al., "Immune-related MicroRNAa are Abundant in Breast Milk Exosomes," Int. J. Biol. Sci. 2012, 8, 118-123.
Del Boccio et al., "A hyphenated microLC-Q-TOF-MS platform for exosomal lipidomics investigations: Application to RCC urinary exosomes," Electrophoresis. 2012, 33, 689-696.
Li et al., "Analysis of the RNA content of the exosomes derived from blood serum and urine and its potential as iomarkers," Philos. Trans. R. Soc. Lond. B Biol. Sci. 2014, 369, May 2, 2013.
Gallo et al., "The Majority of MicroRNAs Detectable in Serum and Saliva Is Concentrated in Exosomes," PLoS One 2012, 7, 30679.
Whiteside, T. L., "Tumor-derived exosomes and their role in cancer progression," Adv. Clin. Chem. 2016, 74, 103-141.
Li et al., "Exosomal microRNA-141 is upregulated in the serum of prostate cancer patients," Onco. Targets Ther. 2015, 9, 139-148.
Lobb et al., "Optimized exosome isolation protocol for cell culture supernatant and human plasma," J. Extracell. Vesicles. 2015, 4, 27031.
Lamparski et al., "Production and characterization of clinical grade exosomes derived from dendritic cells," J. Immunol. Methods. 2002, 270, 211-226.
Momen-Heravi et al., "Current methods for the isolation of extracellular vesicles," Biol. Chem. 2013, 394, 1253-1262.
Tauro et al., "Comparison of ultracentrifugation, density gradient separation, and immunoaffinity capture methods for isolating human colon cancer cell line LIM1863-derived exosomes," Methods. 2012, 293-304.
Van Deun et al., "The impact of disparate isolation methods for extracellular vesicles on downstream RNA profiling," J. Extracell. Vesicles. 2014, 3, 24858.
Clayton et al., "Analysis of antigen presenting cell derived exosomes, based on immuno-magnetic isolation and flow cytometry," J. Immunol. Methods. 2001, 247, 163-174.
Koga et a., "Purification, Characterization and Biological Significance of Tumor-derived Exosomes," Anticancer Res. 2005, 25, 3703-3708.
Mathivanan et al., "Proteomics Analysis of A33 Immunoaffinity-purificed Exosomes Released from the Human Colon Tumor Cell Line LIM1215 Reveals a Tissue-specific Protein Signature," Mol. Cell. Proteomics. 2010, 9, 197-208.
Li et al., "Progress in Exosome Isolation Techniques," Theranostics. 2017, 7,789.
Willms et al., "Cells release subpopulations of exosomes with distinct molecular and biological properties," Sci. rep. 2016, 6, 22519.
Yamada et al., "Comparison of Methods for Isolating Exosomes from Bovine Milk," Clin. Pathol. 2012, 74, 1523-1525.

* cited by examiner

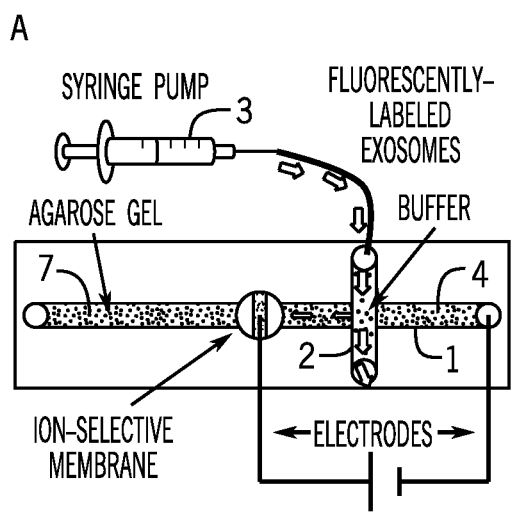
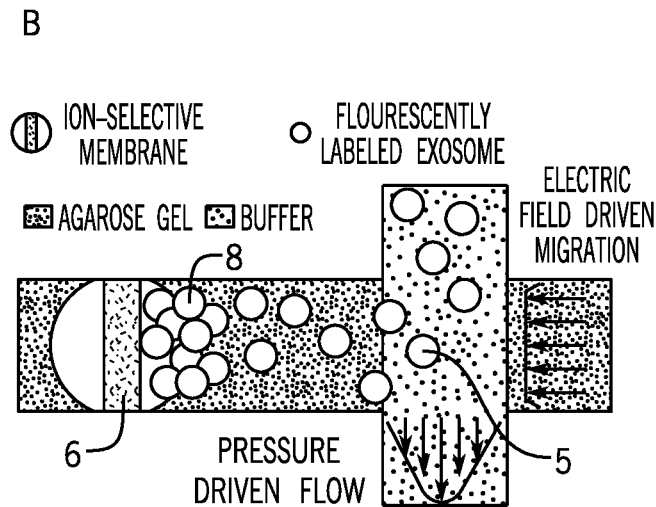
FIG. 1a
FIG. 1b
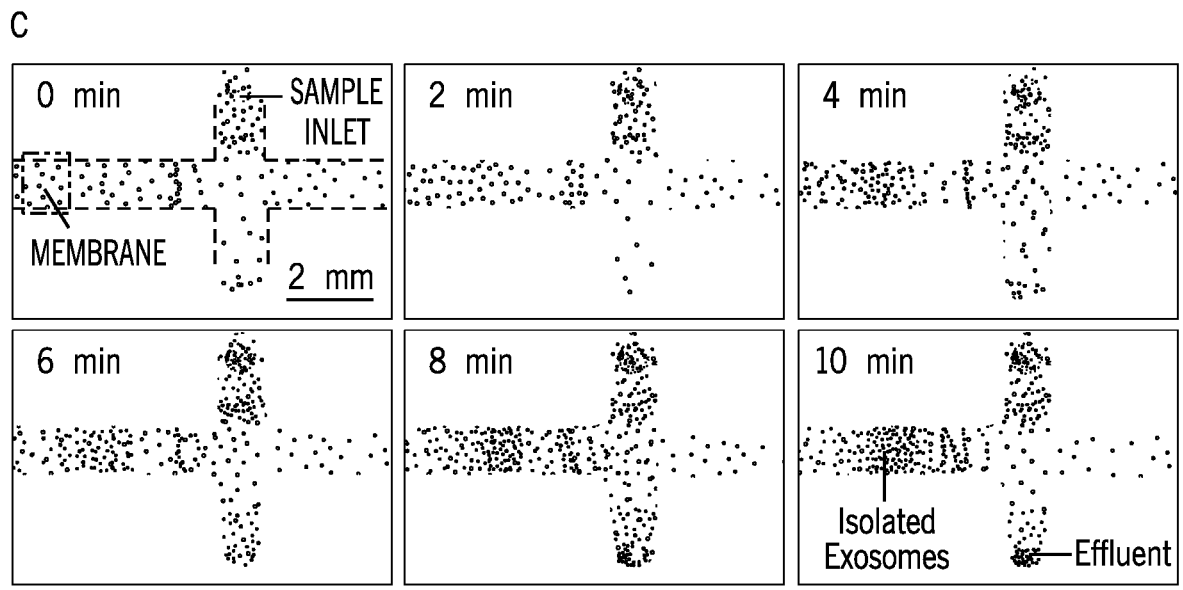
FIG. 1c

SIMULTANEOUS ISOLATION AND PRECONCENTRATION OF EXOSOMES BY ION CONCENTRATION POLARIZATION METHOD AND APPARATUS

RELATED APPLICATION INFORMATION

This application claims the benefit of and is a continuation of U.S. Provisional Application No. 62/637,209, filed Mar. 1, 2018, entitled "Microfluidics for Exosome Concentration" which is incorporated by reference in its entirety.

GOVERNMENT FUNDING STATEMENT

This invention was made with government support under Grant No. R21 AI105361, R21 CA206904 and HG009010 awarded by the National Institute for Health. The government has certain rights in the invention.

FIELD OF THE DISCLOSURE

The present disclosure relates generally to a connector for microfluidic devices and more particularly to a system and method for isolating exosomes.

BACKGROUND OF RELATED ART

In many instances, diagnosis of cancer requires surgical biopsy of a suspected cancerous region. Surgical biopsies are inherently invasive and therefore pose significant risks to patients. This places a limitation on the frequency with which a region can be sampled to check for cancer, and in some cases, the suspected region may even be surgically inaccessible. Additionally, the tissue sampled by a surgical biopsy tends to be a heterogeneous, rather than a homogeneous, representation of the tissue at large thereby leading to ambiguous conclusions. In contrast, liquid biopsies are non-invasive and a variety of biological fluids, such as blood [1, 2], urine [3], saliva [4], and breast milk [5, 6], provide biomarkers indicative of cancer for both diagnostic and prognostic purposes. Biomarkers include cell-free nucleic acids, such as DNA, messenger RNA (mRNA), and microRNA (miRNA) [7-11], circulating tumor cells [12], and extracellular vesicles [13]. In contrast to surgically-derived tissue samples, liquid biomarkers tend to homogenously represent tumor microenvironments. Therefore, they serve as superior identifiers for cancer diagnosis and prognosis, as well as being more cost effective and patient-friendly.

Of particular note in recent years are nanometer-size extracellular phospholipid bilayer vesicles otherwise known as exosomes. Although the exact size range of exosomes has not been fully resolved, they typically fall within the range of 30-150 nm in diameter. They contain proteins on the surface and harbor proteins, mRNA, miRNA, and DNA within. Cells secrete exosomes into the circulatory system, and the exosomes are taken up by adjacent cells and distant cells in other organs. The exact function of exosome function is currently under active investigation and includes altering the extracellular matrix [14, 15], accelerating tumor growth and enhancing metastasis [16-20], imputing drug resistance [21-24], and creating metastatic niches [25-30]. Exosomes form from almost all cell types, and they appear in most types of body fluids such as serum [31, 32], saliva [33], breast milk [34], and urine [35, 36]. Furthermore, the majority of cell-free miRNAs reside within exosomes [37]. This, combined with the fact that the proteins and RNA they carry are specific to the cell of origin, potentially make exosomes and their cargo excellent non-invasive biomarkers [38]. One example of such an exosomal biomarker is miRNA-141, which occurs in prostate cancer patients at expression levels four times higher than that in healthy patients [39]. As another example, Taylor and Gercel-Taylor identified a suite of eight exosomal miRNAs that could potentially act as diagnostic biomarkers for ovarian cancer [31]. Importantly, they concluded that using these biomarkers could potentially differentiate between developing tumors and advanced-stage tumors.

Before analyzing exosomes for useful information, they need to be isolated from their resident media, which is difficult given their small size. The standard method of exosome isolation is ultracentrifugation. The general steps in an ultracentrifugation protocol begin by using submicron filters or low speed centrifugation to remove contaminants such as cell debris, microvesicles, or apoptotic bodies. Subsequently, the exosomes undergo multiple rounds of ultracentrifugation at speeds of 100,000×g or greater to pellet them. Removing the supernatant and then resuspending them in a relatively small volume of buffer produces a concentrated sample useful for investigative purposes [40]. Such high speeds require not only large initial capital costs but also large maintenance and operating costs. In addition to its high expense, ultracentrifugation is a time-consuming and labor-intensive process typically requiring four to six hours of work by a skilled technician or researcher. It is also necessary to culture high volumes (>100 mL) in order to collect enough exosomes for subsequent experiments. In the end, it still does not produce very pure samples and results in yields of only 5-23% [41]. The final exosome sample still suffers from contamination by proteins, and the results tend to be highly variable. Adding a gradient density step, which uses a discontinuous gradient containing different concentrations of sucrose or iodixanol (OptiPrep™), improves the purity of the final sample by separating exosomes from apoptotic bodies, protein aggregates, and nucleosomal fragments based on different flotation densities. However, it adds significantly to the complexity and time required for the process [41-44]. For example, Van Deun et al. found that using an iodixanol gradient reduced protein contamination by more than two-fold, but they also discovered their exosome yield decreased two-fold while ultracentrifugation times increased past twenty hours [44].

An alternative to ultracentrifugation is immunoaffinity capture by magnetic beads and antibody functionalized pillars and packings [31, 45-47]. Immunoaffinity capture works well to isolate exosomes from other fluid components. However, the technique is limited to exosomes with a known antigen. Moreover, the heterogeneity of exosomes produced by cells limits the efficacy of this approach. Studies have revealed that that there is no commonly agreed upon protein that is abundantly expressed on the surface of exosomes derived from diverse origins [48]. Cells release subpopulations of exosomes with unique compositions that elicit a wide range of effects in cells that take them up [49]. Hence, exosome based-diagnostics that use immunoaffinity capture only succeed in isolating a fraction of the exosomes currently present in a patient. Thus, if it is desirable to capture all exosomes, not simply exosomes with a specific antigen, immunoaffinity capture is inadequate. In addition, although the magnetic beads expedite the subsequent analysis of the exosomes, the isolation process is time-consuming and may require more than a day to achieve optimal recovery rates [45].

Yet another isolation technology is commercial precipitation technology like ExoQuick™ and Total Exosome Isolation™. They are attractive because of their simplicity as well as their circumvention of the need to use expensive equipment. However, these kits are still time-consuming as they require overnight incubation. Furthermore, since the reagents in the kits are proprietary, they exhibit contamination from unknown sources leading to discrepancies in their results [44, 50].

Recently, the microfluidics community has started to tackle the problem of exosome isolation. Yang et al. categorized microfluidic isolation techniques into immunoaffinity-based, sized-based, and dynamic microfluidics [51]. Zhao et al. simply transferred the magnetic bead concept to a microfluidic device. They were able to isolate exosomes from 20 μL of blood plasma in 40 min, and they illustrated that exosomes from ovarian cancer patients existed in higher quantities than in healthy control subjects [52]. Vaidyanathan et al. used a combination of immunoaffinity capture and AC dielectrophoresis for the capture of exosomes down to a limit of detection of 2760 exosomes/μL [53]. Chen et al. obtained good purity with their assay as measured by the concentration of RNA per sample volume, but their recovery rates were highly variable ranging from 42-94% [54]. Sized-based microfluidic separations typically rely on microposts inside microchannels thus requiring complex fabrication steps. Wang et al. [55] grew nanowires on their microfluidic posts and captured nanoparticles from 40-100 nm while filtering out cells, proteins, and other cell debris. Davies et al. used pressure driven flow and a porous polymer monolith to isolate exosomes directly from blood yet experienced significant contamination by proteins [56]. Dynamic exosome isolation methods rely on a variety of techniques such as electrophoresis, field-flow fractionation, and acoustic waves. Davies et al. demonstrated direct isolation of exosomes from blood using porous polymer monoliths, varying from 100-1000 nm in pore size, and electrophoresis with field perpendicular to the flow direction. However, the low electric field strength employed in their study allowed them to recover only 2% of exosomes [56]. Another electrophoretic technique developed by Cho et al. applied a higher electric field across a dialysis membrane to achieve a 65% recovery rate in approximately thirty minutes [57]. An acoustic nanofilter in which ultrasound standing waves were applied orthogonally across a continuous sample flow resulted in exosome recovery rates of up to 80% [58]. The current microfluidic technology for exosome isolation varies greatly in terms of yield, sample volume, throughput and operation or fabrication complexity. There is considerable room for improvement. In particular, an isolation device designed to accommodate subsequent analysis such as lysis and detection would be particularly beneficial.

BRIEF DESCRIPTION OF THE DRAWINGS

FIG. 1a is a schematic of the chip is shown in FIG. 1a.

To summarize, FIG. 1b shows a zoomed view of the channels; as the exosomes pass through the intersection of the perpendicular channels, an electric field drives them into the gel where they concentrate at the membrane. FIG. 1c shows a view from below the chip of the exosome isolation process with fluorescently-labeled exosomes In FIGS. 2a-2d, exosomes isolated from a sample of 1×PBS after 10 min using a flow rate of 150 μL/hr and a field strength of 100 V/cm.

Figure 2A:
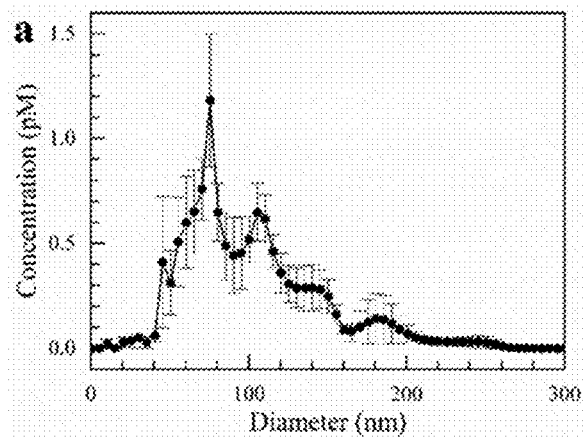
FIG. 2a shows the exosome size distribution before isolation experiments.

In the drawings the parts are numbered:
a first channel—1;
a second channel;—2;
a syringe pump—3;
a medium—4;
an exosome sample—5;
membrane—6;
a filter gel—7; and
an exosome recovery storage area—8.

DETAILED DESCRIPTION

The following description of example methods and apparatus is not intended to limit the scope of the description to the precise form or forms detailed herein. Instead the following description is intended to be illustrative so that others may follow its teachings.

Exosomes carry microRNA biomarkers, occur in higher abundance in cancerous patients than in healthy ones, and because they are present in most biofluids, including blood and urine, can be obtained non-invasively. Standard laboratory techniques to isolate exosomes are expensive, time-consuming, provide poor purity, and recover on the order of 25% of the available exosomes. We present a new microfluidic technique to simultaneously isolate exosomes and preconcentrate them by electrophoresis using a high transverse local electric field generated by ion-depleting ion-selective membrane. We use pressure-driven flow to deliver an exosome sample to a microfluidic chip such that the transverse electric field forces them out of the cross flow and into an agarose gel which filters out unwanted cellular debris while the ion-selective membrane concentrates the exosomes through an enrichment effect. We efficiently isolated exosomes from 1×PBS buffer, cell culture media and blood serum. Using flow rates from 150 μL/hr to 200 μL/hr and field strengths of 100 V/cm, we consistently captured between 60% to 80% of exosomes from buffer, cell culture media, and blood serum as confirmed by both fluorescence spectroscopy and nanoparticle tracking analysis. Our microfluidic chip maintained this recovery rate for more than twenty minutes with a concentration factor of 15 for ten minutes of isolation.

Here we report a new exosome isolation technique that utilizes microfluidic gel electrophoresis and an ion-selective membrane to simultaneously separate and concentrate exosomes from a continuously flowing sample stream. A syringe pump delivers the liquid exosome-containing sample to a channel in a microchip that is arranged perpendicular to the main channel of the chip, which contains agarose gel. The use of electric field to isolate exosomes is reasonable as the electrophoresis of exosomes is independent of its size, as their dimension is much larger than the Debye layer. However, to achieve high throughput isolation out of flowing sample, a large electric field must be used to overcome the large hydrodynamic drag. For a typical Zeta potential of −12 mV and a high throughput linear flow velocity of 0.01 cm/s (or 300 µL/hr in a typical channel of 2 mm×0.5 mm dimension), an electric field of approximately 100 V/cm is required. Such a high field is difficult to introduce into a device with high ionic strength buffers, particularly if it is applied in the longitudinal flow direction, as it will lead to Ohmic heating and bubble generation. This is the main issue in previous attempts on electrophoretic isolation.

As in our earlier work [59-61], we use the ion depletion feature of ion-selective membranes to produce a local transverse field that exceeds the required value without introducing excessive Ohmic heating and bubble formation along the entire flow channel. The depletion zone spans across the flowing stream and into the gel to produce a high transverse field with near-DI water ionic strength locally. Any temperature increase due to Ohmic heating by the intense but narrow transverse electric field is rapidly removed by the flowing solution and bubble formation is never observed. As the exosomes pass through the intersection of the two channels, this electric field drives the exosomes into the gel towards a negatively charged cation exchange membrane. As they are macro-co-ions to the membrane, exosomes concentrate at the membrane surface but do not enter the membrane and are hence enriched in a high ionic-strength zone near the surface of the cation-selective membrane [60, 61, 63]. Additionally, the agarose gel possesses pore sizes on the order of 200-300 nm [62, 63] and filters out larger components such as cells. Both the gel and the membrane also help prevent bubble formation and the creation of a pH gradient within the channel by segregating the electrodes from contact with the interior of the microfluidic channel.

We demonstrate the operation of our device at a high transverse electric field strength (~100 V/cm) and various flow rates and measure the recovery rate of exosomes and the factor by which they concentrate at the membrane. We corroborate our results using particle tracking measurements and reveal our isolated exosomes are in the range of 60 to 130 nm. We envision our isolation chip as the first section of a larger integrated device which will in turn lyse exosomes and then detect the exosomal miRNA content. Previous work by our group illustrated surface acoustic waves (SAW) could lyse exosomes, and our DNA probe-functionalized ion-selective membrane could detect miRNA down to 2 pM [64]. Our aim is to comprise a fully integrated device for the detection of exosomal miRNA for early cancer diagnosis.

Materials

10×PBS (pH 7.4) and 50×TAE (pH 8.4) buffers were obtained from Boston Bioproducts and 150 mM sodium phosphate buffer (pH 7.2) from Teknova. Agarose gels were prepared at 1 wt % in 1×TAE using agarose powder from Ominpur and stored as liquids inside an oven maintained at 65° C. QuikCast polyurethane casting resins (side A and side B) were obtained from TAP Plastics Inc. Acrifix 1R 0192 UV reactive cement was obtained from Evonik Industries while Loctite 3492 light cure adhesive was obtained from Loctite Corporation. Cation-exchange membranes whose fixed negative charge is supplied by organosulfanate groups were provided by Mega a.s (Czech Republic). Carboxyfluorescein succinimidyl ester (CFSE) dye was received from eBioscience.

Exosome Collection and Labeling

AsPC1 cells were grown in RPMI media with 10% fetal bovine serum under standard conditions. Cell-conditioned media was collected, and exosomes were isolated by two different methods: ultracentrifugation and ExoQuick™. For both protocols, cells were initially spun down at 1,200 rpm for three minutes. The cell debris in the supernatant was spun down at 16,500×g for twenty minutes. For the ultracentrifugation protocol, the exosomes were pelleted from 100 mL supernatant by centrifuging at 120,000×g for seventy minutes. For ExoQuick™, the exosomes were collected from 10 mL of the supernatant from the 16,500×g spin according to the manufacturer's protocol. A portion of the exosomes isolated using ExoQuick™ were labeled with CFSE dye. The exosomes were resuspended in 1×PBS and incubated at 37° C. for one hour with 10 µM CFSE.

Chip Fabrication

Referring now to FIG. 1a, Microfluidic chips were fabricated in the same fashion as in previous work [60, 64] from 300 µm polycarbonate sheets in a layer-by-layer fashion. The polycarbonate sheets were sandwiched together and heated in an oven at 170° C. to permanently bond them together. The main channel running along the length of the chip was 2 mm width×30 mm length×500 µm height. A perpendicular cross-channel for delivering exosome samples intersected the main channel at 7.5 mm from the end of the main channel and 7.5 mm from the ion-exchange membrane. The cross channel possessed the same width and height as the main channel but was 5 mm long on either side of the main channel. Fluid inlets with reservoirs to hold buffer were set at the ends of the channel. A 6.9 mm diameter hole was placed in the center of the main channel to hold the membrane cast. Using resin, a steady frame was made for the membrane to adjust for the size difference between the membrane and the hole designed into the PC chip, while providing a free surface to paste the resin frame to the polycarbonate chip utilizing UV glue. A 1.5×1.0×0.3 mm$^3$ (l/w/t) cation-exchange membrane was sealed to the bottom of the cast and remained flush with the top of the microfluidic channel.

Isolation of Exosomes by Gel Electrophoresis

Chips were filled with the liquid agarose gel and used after the gel solidified. The gel was removed from the intersection by displacing it with a 1×TAE buffer before it solidified. A gentle buffer injection through the inlet can push the contents of the cross channel towards the outlet and replace the gel with buffer to provide a gel free path for the exosome sample. The membrane and inlet reservoirs were also filled with 1×TAE buffer and replaced every four minutes after the application of the electric potential. Exosomes were loaded into a 1 mL syringe, and a syringe pump delivered them to the chip at rates of 150 or 200 µL/hr, which is the optimum estimated from the electrophoretic velocity of the exosome under the applied field. After thirty seconds of pumping, electrophoresis was started using a Keithley 2400 Sourcemeter as the voltage source and platinum electrodes in the membrane and electrode inlet reservoirs. The field strength for all experiments was 100 V/cm. For experiments where the exosomes were to be analyzed by nanoparticle tracking, gel electrophoresis was typically performed for ten minutes. For the particle tracking measurements, a chip with a removable bottom was used. The gel, from the cross channel to the membrane, was removed and placed in 50 μL 1×TAE. The effluent and the gel were placed into an oven at 70° C. for fifteen minutes. The samples of exosomes collected from the chips were then diluted in 1×TAE between 100 and 5000-fold depending on the original media. They were stored at −20° C. prior to measurement by a Malvern NanoSight NS300. For each nanoparticle tracking sample, there were five runs for sixty seconds each using an injection rate of 30 μL/min.

For exosomes isolated from cell media and blood serum, isolation experiments were conducted with five replicates. Human whole blood and human recovered plasma were purchased from Zen-Bio Inc. (Research Triangle Park, N.C., USA). Fresh whole blood and serum was collected in 10 mL heparin-coated Vacutainer tubes and shipped following testing. Upon arrival, the blood and serum were stored at 4° C. prior to use.

Exosome recovery rates were analyzed quantitatively using fluorescently-labeled exosomes. Two flow rates, 150 μL/hr and 200 μL/hr, were analyzed by collecting the effluent at 10 min intervals for a total of 20 min. Fluorescence was measured using a Tecan Infinite M200 Pro.

Device Operation

We adapted and altered the microfluidic device we previously used for the quantification of nucleic acids by nanoparticle aggregation in references [59] and [60] to the isolation of exosomes. Zeta potential measurements revealed the zeta potential of the exosomes to be −12±3 mV which is comparable with previous measurements from the literature [65]. However, we emphasize the importance of the buffer pH on zeta potential since previous reports indicate zeta potential of bodily components such as red blood cells will change under the influence of pH [66]. The negative electrical charge of the exosomes indicates they can be driven by an electric field as also demonstrated by others [56, 57].

In our present setup, a syringe pump transports a sample of exosomes in 1×PBS buffer to the microfluidic chip. As the exosomes flow through the intersection of the perpendicular channels, the electric field drives migration of the exosomes into the agarose gel towards the membrane. The gel, which possesses pore sizes of approximately 200-300 nm [62, 63], prevents large particles such as cells from entering the gel. The continuous flow from the pump eliminates clogging of the gel by washing away these larger particles. The exosomes migrate towards the membrane, but the negative charges on the membrane prevent them from passing through it. The effect creates a region where the exosomes continuously concentrate, thus trapping them inside the gel. Another feature which is essential to our device is the segregation of the electrodes from the microfluidic channel by use of the gel and the membrane. The high potentials used to create the strong electric fields generate a significant amount of bubbles. Both the gel and the membrane prevent these bubbles from entering the microfluidic channel and interfering with the electric field-driven migration of the exosomes. Furthermore, the high potentials create high concentrations of hydrogen and hydroxide ions in the membrane reservoir and in the gel inlet reservoir, respectively. This effect leads to the creation of a powerful pH gradient which could affect the zeta potential of the exosomes and thus their direction of migration. Therefore, it is necessary to exchange the buffer in the reservoirs every few minutes either by replacing the entire solution all at once or by supplying a continuous stream of fresh buffer into the reservoirs. The result of this setup is the isolation and preconcentration of exosomes as illustrated by FIG. 1.

Confirmation of Exosome Isolation

Figure 2B:
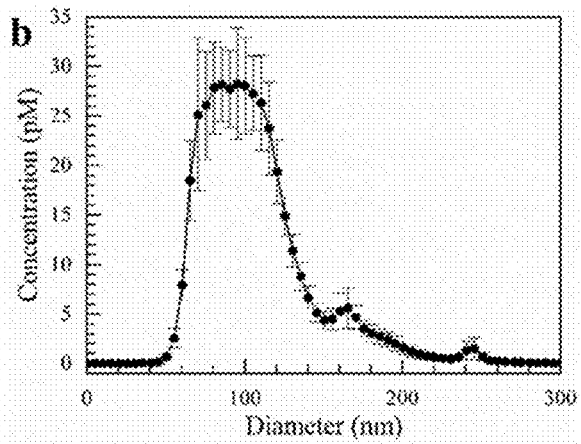
FIG. 2b shows size distribution of the exosomes collected from the gel. c) Size distribution of the exosomes in the effluent.
Figure 2C:
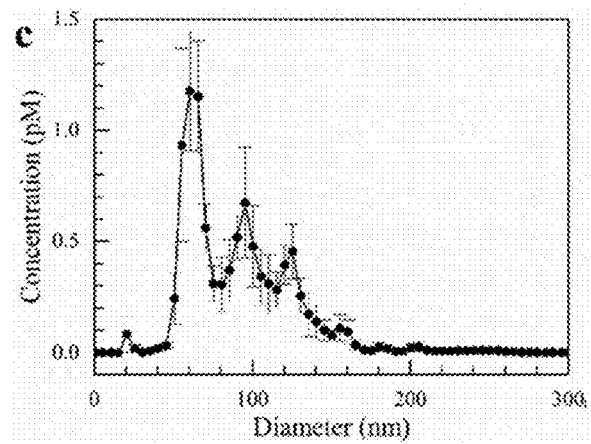
FIG. 2c shows error bars represent the standard error with n=5.

In order to confirm we efficiently captured exosomes within the gel, we compared the contents of the gel and the sample effluent with the initial exosome sample using nanoparticle tracking measurements. Using a nominal electric field strength of 100 V/cm, we pumped exosome sample into the chip at a rate of 150 μL/hr for 10 min. Subsequently, we analyzed the number of exosomes in the sample before isolation, in the gel after isolation, and the effluent by nanoparticle tracking. FIGS. 2a-c display the results. We obtain an approximate concentration of the total number of exosomes using the known solution volume by summing the concentration of particles at each diameter, in increments of 1 nm, from 0 to 150 nm. Although exosomes typically fall below 150 nm, we include the concentration for particles up to this point to account for possible aggregates composed of multiple exosomes. At 150 μL/hr, based on the measured concentrations and the known volumes of the gel isolation region and the effluent, we achieve a recovery rate of approximately 70%. The recovery rate was estimated by the ratio of (exosomes in gel)/(total amount of exosomes in inlet). It is possible that we may not remove all the exosomes from the gel, so our recovery may be somewhat of an underestimate. Significantly, the concentration measured from the gel is much higher than the concentration measured in the inlet. This clearly demonstrates not only that we capture exosomes within the gel but also that we concentrate them as well. Notably, the size distribution of the sample from the gel displayed in FIG. 2b illustrates most of what we capture is around 150 nm or less which is the reported size range for exosomes. The size distributions of the original exosome sample in FIG. 2a and the exosomes isolated in the gel in FIG. 2b are relatively similar as well. This is clear confirmation of exosome capture.

Quantitative Fluorescence Evaluation of Exosome Isolation

We extended the above experiments of isolating exosomes to using flow rates of 0.15 and 200 μL/hr and a field strength of 100 V/cm but analyzed the effluent quantitatively using fluorescence. We estimated the concentration of the original exosome sample using nanoparticle tracking to be 71±7 pM. Then we created a calibration curve from 0.015-0.71 pM based on dilutions of the original sample. For the actual isolation experiments conducted with the microfluidic chip, we diluted the original sample of CF SE-dyed exosomes by a factor of ten. We collected the effluent at intervals of 10 and 20 min and determined the exosome concentration by fluorescence with the results reported in FIG. 2d. The fluorescence of the exosomes in the effluent was measured and the recovery rate was determined by the (total amount of exosomes in inlet−amount of exosomes in effluent)/(total amount of exosomes in inlet). The recovery rates range from 60 to 76%, but the large standard deviation at each flow rate and time interval indicates there is also much overlap. Looking at all the values, the average and standard deviation of the recovery rates is 69±7%, consistent with the nanoparticle tracking measurements discussed in Section 3.2.

Figure 2D:
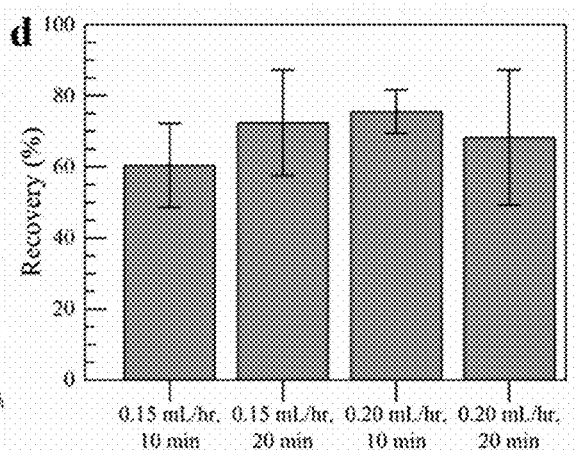
FIG. 2d shows quantitative exosome recovery as measured by the fluorescence of exosomes labeled with CFSE dye.

Importantly, FIG. 2d shows that the recovery rate, within error, is the same at the 10 and 20 minutes collection times. This indicates the capacity of the gel to collect exosomes is not restricted in at least a 20 minutes time interval. Although longer times might eventually overcome the capacity of the gel to take in more exosomes, extending the length or width of the gel region would restore its capacity to capture more exosomes. However, it may be advantageous to keep the gel region as small as possible. The reason is that a small gel region maximizes the concentration of the exosomes. Based on our chip dimensions, if we approximate the volume the exosomes are confined to as 7.5 µL (7.5 mm×0.5 mm×2 mm), then after 20 minutes of isolation time, the concentration of our exosomes is a factor of 30 higher than the original exosome concentration. Another way to put it is that, at the given field strength and flow rate, the exosomes concentrate by a factor of 15 every 10 min.

The preconcentration of exosomes may prove to be critical for early cancer detection assays which rely on either the detection of exosomes themselves or on the detection of exosomal RNA. The detection limits of such assays are measured in concentrations and not exosome numbers. For example, Zhao et al. successfully detected exosomes for ovarian cancer down to $7.5 \times 10^5$ particles/mL, but it was unclear at which stage of cancer their diagnostic chip would be useful [52]. Similarly, Vaidyanathan et al.'s nanoshearing technique could specifically detect exosomes from breast cancer patients down to $2.8 \times 10^6$ particles/mL, but it was again unclear at which stage of cancer this technology would be viable [53]. If cancer screening requires detection limits lower than these exosome concentrations, preconcentration is required. This concentration effect could also be particularly beneficial for potential downstream analysis of the exosome cargo. To date, there is no consensus as to the number of miRNA, for example, that exosomes may contain, ranging from 0.001-10 copies, and thus concentrating the exosomes could improve detection of miRNA that are at very low copy numbers [67-69]. This will depend on how this device is coupled to downstream lysis and detection technologies, but this preconcentration aspect, in addition to the isolation capacity, also holds promise.

Comparison with Ultracentrifugation and ExoQuick™

Figure 3A:
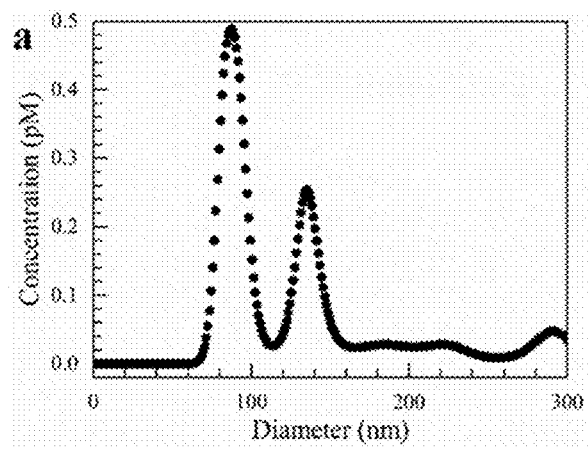
FIG. 3a shows single capture from NanoSight of cell culture media before isolation.

Next, we isolated exosomes directly from cell culture media and then also made a direct comparison to the methods of ultracentrifugation and ExoQuick™ precipitation. Following the same procedure as above using our microfluidic chip, we determined the exosome recovery rate to be 80±11%. Again, our results in FIG. 3 appear similar to those presented above. We avoid significant concentrations of particles with diameters above 300 nm. The size distribution of the exosomes from the cell media culture is similar to the one from 1×PBS. Comparing FIGS. 3b to 3d, the gel clearly recovers the exosome peak at 83 nm. However, it does not seem to recover the peak at 130 nm very well. This could be because the exosomes 130 nm in diameter have a lower mobility in the electric field and also because of a sieving effect by the gel. Therefore, the 83 nm exosome concentration enhances in the gel relative to the 130 nm exosomes, and the peak tends to smooth out at larger diameters. We also show a single capture from the nanoparticle tracking analysis before and after isolation in FIGS. 3a and 3c because the averaging performed by the NanoSight tends to smooth out the peaks. In FIG. 3c, we do see a shoulder at 120 nm which illustrates there is still capture of larger exosomes.

For comparison, we isolated one sample of exosomes from cell culture media by ultracentrifugation and another sample by ExoQuick™. Based on triplicate measurements of these samples using nanoparticle tracking analysis, the recovery rates were 6% and 30% with standard deviations of 2% and 11%, respectively—far lower than the 80% recovery achieved with our microfluidic chip.

Our new isolation methodology possesses a number of advantages over these traditional laboratory techniques. First, it does not require nearly as much sample volume to carry out the isolation protocol. Ultracentrifugation required more than 100 mL and ExoQuick™ more than 10 mL to produce a useful concentration of exosomes in only 500 µL of PBS. Furthermore, ultracentrifugation entails more than an hour of operating time while ExoQuick™ requires overnight incubation. Our microfluidic chip needs less than 100 µL for operation and can process 200 µL with good recovery rates in one hour. The recovery rate in our microfluidic chip is more than 10-fold higher than that from ultracentrifugation and more than 2-fold that of ExoQuick™. Finally, there are substantial differences in costs between these techniques. Not only does ultracentrifugation have high capital costs, but it has high operating costs as well. ExoQuick™ is much less expensive, but it still carries with it the costs associated with the repetitive use of reagents. The microfluidic technique we developed requires no more than a syringe pump and a voltage source in addition to the chip itself, and it runs using common laboratory reagents.

Isolation from Biological Samples

To prove the utility of our platform to the application of expected clinical and laboratory samples, we tested the capability of our microfluidic device to isolate exosomes from blood serum. We demonstrated the isolation capability by first spiking a blood sample with exosomes isolated using ExoQuick™ and then removing the red blood cells by centrifugation. We performed exosome isolation for 10 min using our microfluidic chip at a flow rate of 150 µL/hr and an electric field strength of 100 V/cm. As we did previously, we collected the effluent and excised the gel to extract the exosomes. Following dilution, we measured their approximate concentrations using nanoparticle tracking with the size distributions displayed in FIG. 4. The measured recovery rate was 77±14% within a 95% confidence interval.

Figure 4A:
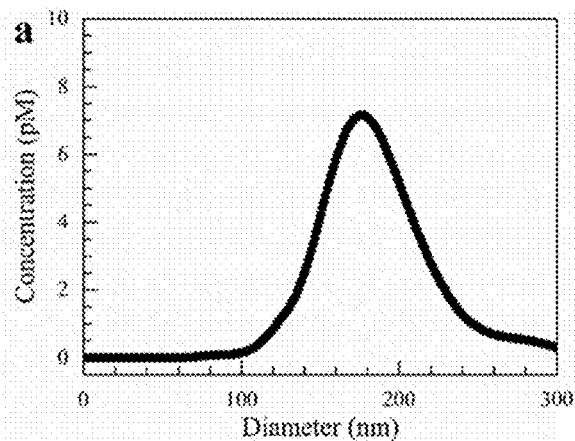
FIG. 4a shows inlet single capture size distributions for exosomes from blood serum.
Figure 4B:
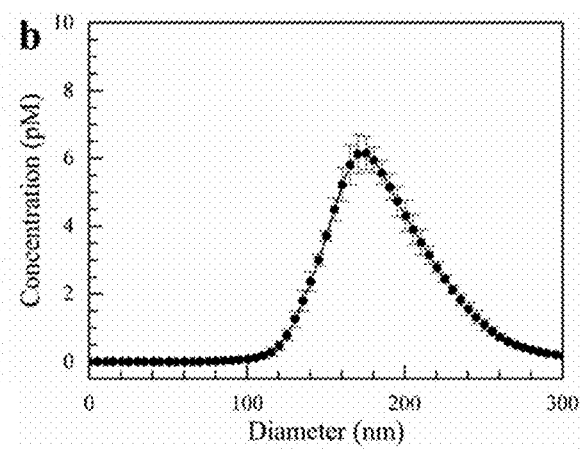
FIG. 4b shows inlet average size distributions for exosomes from blood serum.
Figure 4C:
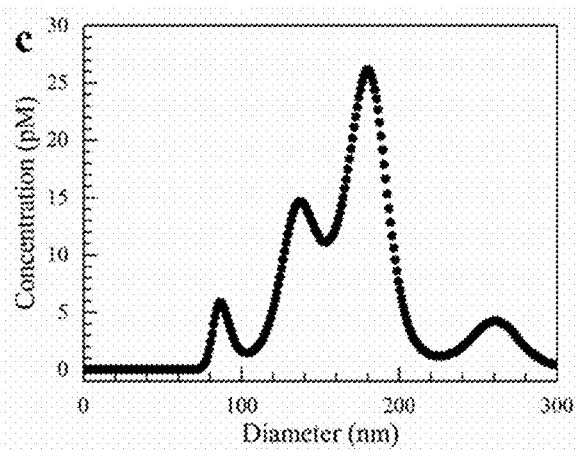
FIG. 4c shows gel single capture size distributions for exosomes from blood serum.
Figure 4D:
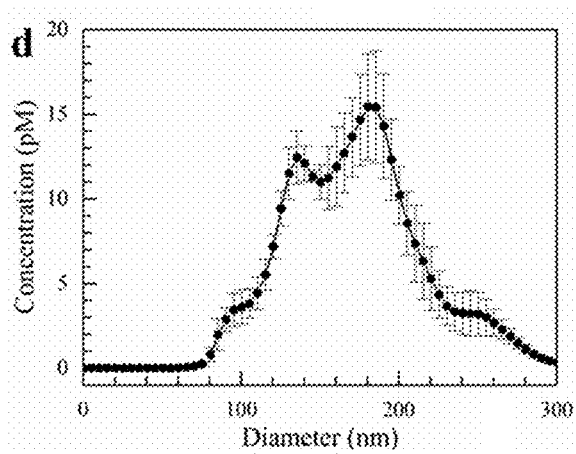
FIG. 4d shows gel average size distributions for exosomes from blood serum.
Figure 4E:
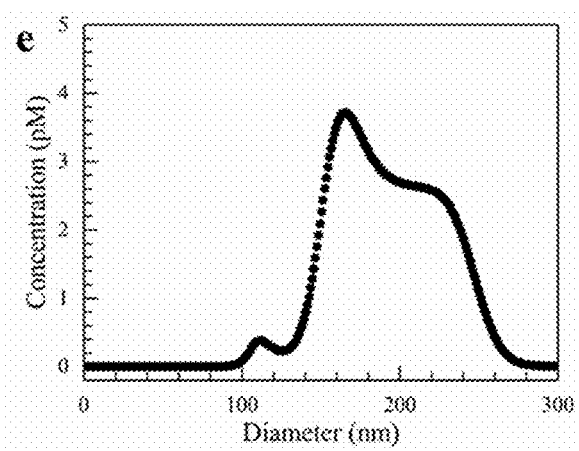
FIG. 4e shows effluent single capture size distributions for exosomes from blood serum.

In order to obtain a clearer picture of what is happening, it is once again instructive to examine the single capture graphs in FIGS. 4a, 4c, and 4e, as opposed to the average graphs. The individual captures better illustrate the various peaks within the different size distributions. FIG. 4a clearly shows the blood serum contains a Gaussian-shaped distribution of particles from approximately 100 to 300 nm with a peak maximum at 180 nm. On the other hand, the spiked exosomes, whose size distribution is shown in FIG. 3a, are not readily apparent as the 80 and 120 nm peaks are obscured due to the greater concentration of what are most likely microvesicles. However, in FIG. 4c where we examine the particles captured by the gel, the spiked exosome peaks reappear. Although the 180 nm peak still possesses the highest concentration, the concentrations of the 90 and 120 nm peaks increase substantially relative to the 180 nm one. On average, the ratio of concentration at 180 nm to the concentrations at 90 decreased from approximately 41 to 5.2 after capture within the gel. Furthermore, in FIG. 4e, there is a significant rightward shift in the size distribution as well as a relatively clean cutoff below about 130 nm in the effluent. This is evidence of a strong sieving effect by the gel. In addition, the cutoff below 130 nm in the effluent is important since it demonstrates we are capturing most of the particles in the exosome size range.

We developed a simple microfluidic device to continuously isolate exosomes by trapping them in agarose gel using an ion-selective membrane. We procured intense but narrow transverse electric fields by segregating the electrodes from the microfluidic channel using the gel and the membrane, and we deterred the effect of large pH changes by refreshing the buffer in the electrode reservoirs. We also prevented Ohmic heating and bubble generation by the high sample flow rate through the narrow region with the high transverse electric field. Our system proved capable of isolating greater than 70% of the incoming exosomes at 150 µL/hr for at least 20 min. We could further improve the throughput of our assay by using higher sample flow rates. Such higher flow rates could be accommodated with multiple parallel channels. Alternatively, although the capture efficiency might go down with one channel, introducing a recycle stream or passing the sample downstream through another channel would be an effective means to capture nearly all the exosomes. Nanoparticle tracking analysis confirmed a sieving effect produced by the gel which significantly enriched the exosome population relative to the microvesicle population. We could further enhance this effect by optimizing the pore size of the gel which can be adjusted by changing the agarose concentration. Decreasing the pore size will lead to a purer exosome sample. In addition, the nanoparticle tracking analyses demonstrated superior recovery of our technique compared to the conventional techniques of ultracentrifugation and ExoQuick™: 60-80% versus 6% and 30%, respectively.

Not only does our isolation scheme prove useful over the traditional ultracentrifugation and ExoQuick™ precipitation techniques, but it also adds to the suite of microfluidic technologies developed for exosome isolation and recovery. Our device is particularly valuable for a few reasons. First, it not only isolates exosomes, but it concentrates them as well which may prove to be a critical feature for early stage cancer detection. This may be necessary if exosomes themselves act as the biomarkers, but it may also be required if it is the exosomal RNA used for biomarker detection. Our setup combines preconcentration with isolation. Second, our setup can easily integrate with other microfluidic unit operations such as thermal or SAW lysis and miRNA detection by the current-voltage characteristics of ion-selective membranes [64] or the nucleic acid detection scheme we developed previously [59, 60]. The ability to isolate, lyse, and then detect in a single fully integrated device would be a major advancement in the field of point-of-care diagnostics. Third, we avoid clogging of the pores of the membrane because of its ion-selective nature. Unlike an uncharged membrane, our negatively charged membrane repel the exosomes which prevents them from blocking the pore entrances at the surface of the membrane, thus utilizing the external ion concentration polarization phenomenon of the cation-selective membrane to enrich the exosome macroions. Finally, we clearly established the applicability of our device to clinical samples by demonstrating the recovery of exosomes from both blood serum and cell media culture.

To summarize, a schematic of the chip is shown in FIG. 1a. FIG. 1b shows a zoomed view of the channels; as the exosomes pass through the intersection of the perpendicular channels, an electric field drives them into the gel where they concentrate at the membrane. FIG. 1c shows a view from below the chip of the exosome isolation process with fluorescently-labeled exosomes.

In FIGS. 2a-2d, exosomes isolated from a sample of 1×PBS after 10 min using a flow rate of 150 µL/hr and a field strength of 100 V/cm. FIG. 2a shows the exosome size distribution before isolation experiments. FIG. 2b shows size distribution of the exosomes collected from the gel. c) Size distribution of the exosomes in the effluent. FIG. 2c shows error bars represent the standard error with n=5. FIG. 2d shows quantitative exosome recovery as measured by the fluorescence of exosomes labeled with CFSE dye. The effluent was collected at 10 min intervals for two different flow rates using a constant field strength of 100 V/cm. The error bars are standard deviations with n=3.

Figure 3B:
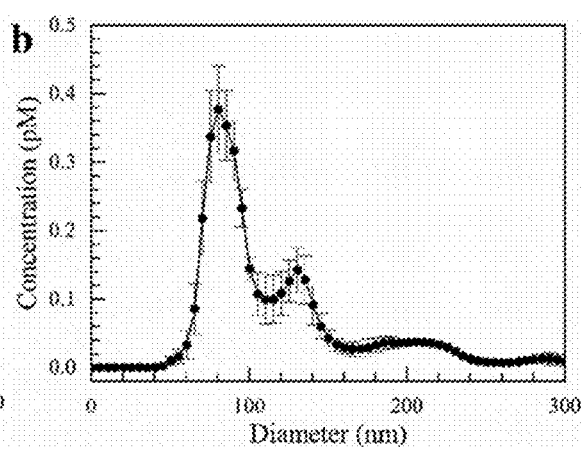
FIG. 3b shows average size distribution of cell culture media before isolation.
Figure 3C:
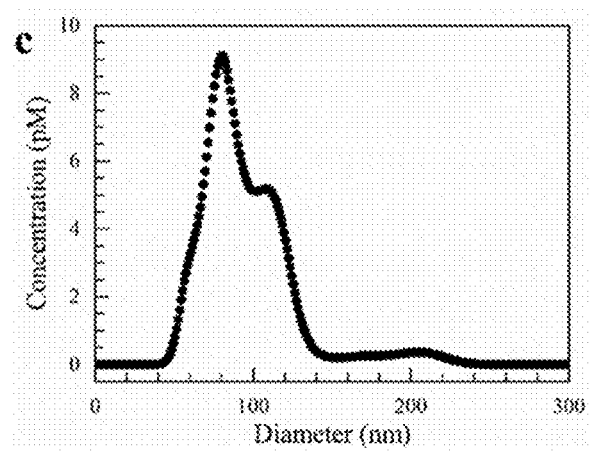
FIG. 3c shows single capture from NanoSight of exosomes isolated in gel.
Figure 3D:
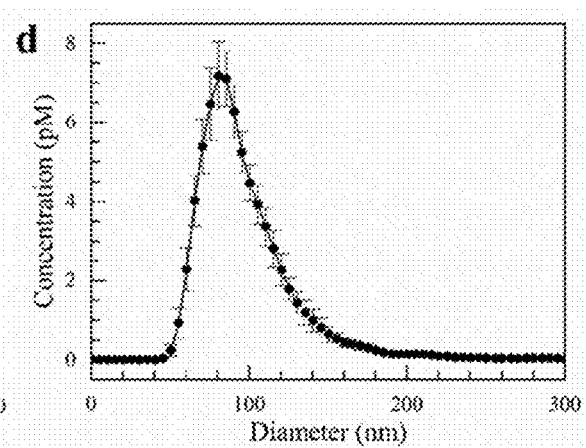
FIG. 3d shows average size distribution of exosomes isolated in gel. Error bars represent the standard error with n=5.

In FIGS. 3a-3d, exosomes isolated directly from cell culture media using our microfluidic chip after 10 min with a flow rate of 150 µL/hr and an electric field of 100 V/cm. FIG. 3a shows single capture from NanoSight of cell culture media before isolation, FIG. 3b shows average size distribution of cell culture media before isolation. FIG. 3c shows single capture from NanoSight of exosomes isolated in gel. FIG. 3d shows average size distribution of exosomes isolated in gel. Error bars represent the standard error with n=5.

Figure 4F:
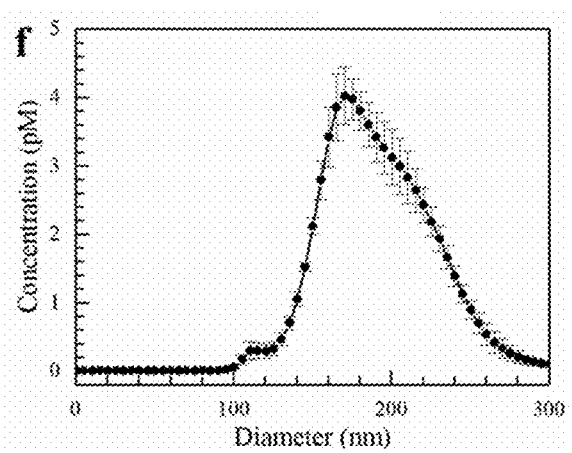
FIG. 4f shows effluent average size distributions for exosomes from blood serum.

In FIGS. 4a-4f, size distributions for exosomes from blood serum are shown. The flow rate was 150 µL/hr, and the field strength was 100 V/cm. FIG. 4a shows inlet single capture. FIG. 4b shows inlet average. FIG. 4c shows gel single capture. FIG. 4d shows gel average. FIG. 4e shows effluent single capture. FIG. 4f shows effluent average. Error bars represent the standard error with n=5.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents.

We claim:

1. A method of simultaneous isolation and preconcentration of exosomes by ion concentration polarization comprising
   providing a sample medium including exosomes with microRNA biomarkers;
   separating a first portion of the sample from a second portion of the sample with an ion-depleting ion-selective membrane wherein the membrane generating a high transverse local electric field;
   delivering pressure-driven flow to move the medium bearing the exosome sample to the membrane;
   separating the exosome sample from the medium in the transverse electric field into a filter gel to remove debris; and
   simultaneously isolating exosomes and preconcentrating them by electrophoresis;
   wherein the ion-selective membrane concentrates the exosomes through an enrichment effect.

2. The method of claim 1 wherein the medium is a biofluid.

3. The method of claim 2 wherein the biofluid is either blood and urine.

4. The method of claim 1 wherein the filter gel is an agarose gel.

5. The method of claim 1 wherein the medium is at least one of 1×PBS buffer, cell culture media and blood serum.

6. The method of claim 1 wherein the flow has a flow rate between 150 µL/hr to 200 µL/hr.

7. The method of claim 1 wherein field strengths of 100 V/cm.

8. The method of claim 1 further comprising with a concentration factor of 15.

9. The method of claim 1 wherein the recovery rate for more than twenty minutes for ten minutes of isolation.

10. The method of claim 1 wherein at least 60% to 80% exosomes are consistently captured.

11. The method of claim 1 wherein the ion-selective membrane concentrates the exosomes through an enrichment effect.

12. A microfluid chip comprising: a first channel and a second channel transverse to the first; a syringe pump configured to create a pressure-driven flow of a medium including an exosome sample through the first channel; an ion-depleting ion-selective membrane configured to generate a high transverse local electric field positioned in the flow positioned at the intersection of the first and second channels, which separates the exosome sample from the medium; a filter gel to remove debris from the separated exosome sample; and an exosome recovery storage area containing the separated exosome sample located in the second channel.

13. The microfluidic chip of claim 12 wherein the chip simultaneously isolates and preconcentrates exosomes by electrophoresis.

14. The microfluidic chip of claim 12 wherein the membrane repels the exosome sample in order to prevent the exosome sample from blocking a series of pore entrances at the surface of the membrane.

15. An integrated microfluidic device comprising a lysing means; and a exosomal detecting means, wherein the exosomal detecting mean is configured to simultaneously isolate exosomes and preconcentrate exosomes by electrophoresis.

16. An integrated microfluidic device of claim 15 wherein the lysing means uses surface acoustic waves.

* * * * *